United States Patent [19]

Koch et al.

[11] Patent Number: 4,501,919
[45] Date of Patent: Feb. 26, 1985

[54] PROCESS FOR THE PRODUCTION OF SERINE DERIVATIVES

[75] Inventors: Melvin V. Koch, Milan; Ambrogio Magni, Osnago-Como, both of Italy

[73] Assignee: Gruppo Lepetit S.p.A., Italy

[21] Appl. No.: 152,447

[22] Filed: May 22, 1980

[51] Int. Cl.$^3$ .......................................... C07C 51/353
[52] U.S. Cl. .................... 562/437; 562/444; 562/445; 562/567; 562/570; 544/237; 544/336; 546/147; 546/170; 546/335; 548/531; 549/76; 549/496
[58] Field of Search ............... 562/444, 445, 567, 570, 562/437; 544/237, 336; 546/147, 170, 335; 548/531; 549/496, 76

[56] References Cited

U.S. PATENT DOCUMENTS 3,992,432 11/1976 Napier ............................ 260/465.1

FOREIGN PATENT DOCUMENTS 839500 5/1952 Fed. Rep. of Germany ...... 562/440
1086242 1/1961 Fed. Rep. of Germany ...... 562/440
1140198 11/1962 Fed. Rep. of Germany ...... 562/440
1017396 12/1952 France ................................ 562/440

OTHER PUBLICATIONS

Jones, Aldrich Chimica Acta, 9, 35 (1976).
Dehmlow, Enc. of Chem. Tech., vol. 5, pp. 62–69, 3rd ed., (1980).
Erlenmeyer et al., Liebigs Annalen der Chemie 284 36, (1895).

Primary Examiner—Robert Gerstl
Attorney, Agent, or Firm—William J. Stein; Stephen L. Nesbitt; Ronald G. Brookens

[57] ABSTRACT

Serine derivatives are synthesized by the condensation of an alkali metal salt of a glycine derivative and a carbonyl compound in the presence of a phase transfer catalyst.

10 Claims, No Drawings

PROCESS FOR THE PRODUCTION OF SERINE DERIVATIVES

The invention concerns a new process for the production of serine derivatives. More particularly the present invention relates to a process for the production of a serine derivative of the formula

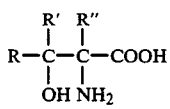

wherein R stands for phenyl, substituted phenyl such as methylphenyl, methoxyphenyl, ethoxyphenyl, halogenophenyl, hydroxyphenyl, acetylphenyl, nitrophenyl, cyanophenyl, biphenylyl, sulfamoylphenyl, and methylsulfonylphenyl, tert-alkyl such as tert-butyl or a heteroaromatic mono- or bi-cyclic radical such as pyrrolyl, thienyl, furyl, pyridinyl, pyrazinyl, quinolinyl, phthalazinyl and the like. R' represents hydrogen or ($C_1$–$C_4$) alkyl and R" is hydrogen, ($C_1$–$C_4$)alkyl or phenyl.

The process described in the present invention can suitably be employed for the preparation of threophenylserine, threo-p-nitrophenylserine, threo-p-acetylphenylserine and threo-p-methylsulphonylphenylserine which are used, for instance, as starting materials for the production of known antibiotic substances such as chloramphenicol, thiamphenicol and cetophenicol.

It is known since 1895 that phenyl-serine and homologues of this compound can be prepared by condensing glycine with an aromatic aldehyde in alkaline solution (Liebig's Annalen der Chemie, Vol. 284 (1895), pages 36 et seq.)

Thus for example benzaldehyde can be condensed with glycine in an aqueous sodium hydroxide solution yielding first a benzylidene phenylserine and, after acid hydrolysis, the desired phenyl serine. Several other processes are known in the literature for the preparation of phenyl- and p-nitrophenyl-serine, such as for instance those described in German Pat. Nos. 839,500 and 1,086,242 wherein the condensation reaction is carried out in aqueous alcohol in the presence of alkaline earth hydroxides, such as calcium hydroxide, as condensing agents. Other methods are known which generally involve as the first reaction step, the formation of an intermediate Schiff's base of glycine with an aldehyde, which is subsequently condensed in aqueous alcohol with the suitably selected aromatic aldehyde. Treatment of the condensation product with mineral acids then affords the desired phenylserine derivative (see for instance German Pat. Nos. 960,722 and 1,140,198 and French Pat. No. 1,017,396).

It has now been found, according to the present invention, that serines may be prepared in an improved manner by condensing an alkaline salt of glycine dissolved in an aqueous solution of an alkali metal hydroxide with a suitably selected carbonyl compound located in an organic phase in the presence of a suitable catalyst according to the "phase-transfer catalysis" techniques. Phase-transfer catalysis is a new method in preparative organic chemistry in which substances located partly in an aqueous and partly in an organic medium are made to react in the presence of suitable catalysts. This new method has been developing very fast in the last few years but up to now no example of an aldol-type condensation, as described in the present invention, has been reported.

The process described in the present invention has considerable advantages over the conventional methods known in the prior-art and namely:

increased yields, which on the average range from 80 to 90, and even more, percent while in the prior-art processes they are generally lower than 80%. As an example in German Pat. Nos. 839,500 and 960,722, the yields amount to about 50%, in German Pat. No. 1,086,242 to about 75% and in French Pat. No. 1,017,396 to about 78%, handling of less dangerous materials, since for instance the use of alcoholic solvents generally employed in the prior-art reactions, can be avoided, and simpler workup which does not involve time-consuming operations.

More particularly the process described in the present invention runs through the following scheme:

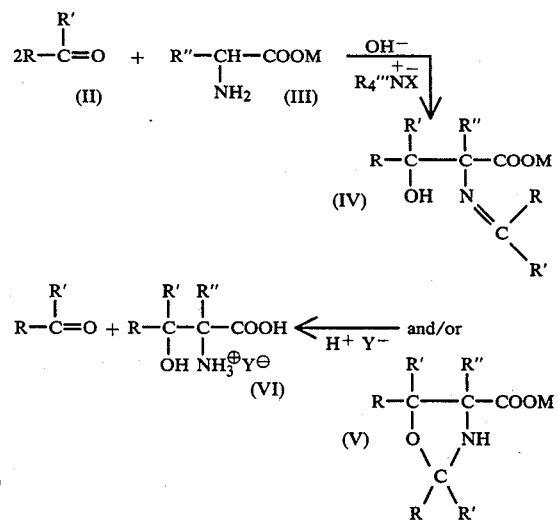

wherein

R, R' and R" are as defined before;

M stands for an alkali metal such as sodium, lithium or potassium;

each of the four radicals R''', which may be equal or different, represents an alkyl residue containing from 1 to 20 carbon atoms and the anion $X^-$ represents a normal anion deriving from inorganic or organic acids such as chloride, iodide, bromide, hydrogen sulfate, perchlorate, nitrate, acetate, benzoate, p-toluensulfonate, naphthalenesulfonate and the like.

Suitable quaternary ammonium salts which may be employed in the process of the invention are for instance methyltributylammoniumchloride, methyltributylammonium iodide, tetrabutylammonium hydrogen sulfate, methyltrioctylammonium chloride (tradename of technical-grade, not entirely uniform product Andogen 464 ®), decyltriethylammonium bromide, hexyltriethylammonium bromide and the like. $H^+ Y^-$ stands for mineral acid.

The molar ratio of the reaction partners i.e., the carbonyl compound of formula II and the glycine salt of formula III is 2 to 1 respectively, as the first step of the reaction is the formation of a Schiff's base; however, the excess of carbonyl compound which, as described in the above scheme, is regenerated by acid hydrolysis, can be easily recovered at the end of the reaction and recycled.

The amount of phase-transfer catalyst employed may range between wide limits, but balancing the facts that the reaction rate is proportional to the amount of catalyst and that large amounts of catalyst may provoke undesired side reactions which lower the yields, it is preferably employed between about 5 and 10 mol % catalyst.

The concentrated alkali metal hydroxide is generally employed at least in molar ratio to the catalyst. However, it may be convenient to prepare the glycine alkaline salt directly in situ from glycine and the selected alkali metal hydroxide; in these cases the alkali metal hydroxide is employed at least in molar ratio to the glycine substrate plus the catalyst.

According to the phase-transfer catalysis technique one of the reactants, in this case the glycine salt, is dissolved in water and preferably in the minimal amount of water as it is usually optimum for PCT that working concentrations should be as high as possible, and its reaction partner, in this case the carbonyl compound, is dissolved in the organic phase. The organic solvent, named co-solvent, which is employed in this reaction must be selected with particular care taking into consideration the following facts:

according to the liquid-liquid phase-transfer catalysis conditions the co-solvent must substantially be immiscible with the aqueous phase; however in the present case it has to be considered that the aqueous phase is a very salted solution containing the glycine salt and the alkali metal hydroxide and that therefore also solvents partially miscible with water, such as for instance tetrahydrofuran or dioxane, can suitably be employed;

it should be unreactive in the presence of concentrated aqueous alkalis; for instance chloroform which is considered the solvent of choice in several phase-transfer reactions, should not be used in this case because it reacts with the alkali metal hydroxide in the presence of the phase-transfer catalyst yielding the very reactive and undesired dichlorocarbene; and finally it should not inhibit the reaction; it has been found in fact that some solvents such as for instance nitrobenzene and some alcohols surprisingly inhibit phase-transfer reactions (see J. Dockx. Quaternary ammonium compounds in organic synthesis—Synthesis 1973, 441-456).

Solvents which may suitably be employed are therefore methylene chloride, dioxane, tetrahydrofuran, toluene, benzene, chlorobenzene, carbon tetrachloride, and other organic solvents that comply with the above requirements.

The temperature of the reaction, which generally is completed in from 4 to 8 hours, is kept between 0° and 25° C. and preferably between 5° and 10° C.

More particularly the reaction of the present invention is carried out by stirring a concentrated aqueous solution of the glycine salt of formula III and an alkali metal hydroxide, into a cooled organic solution of the carbonyl compound of formula II containing the selected phase-transfer catalyst. The addition may take from 5 minutes to 5 hours, however, preferably it is carried out in 3-4 hours. Stirring at low temperature is prolonged until the reaction is completed and then an aqueous solution of a strong mineral acid and preferably aqueous hydrochloric acid, is added to the reaction mixture which is moderately heated. Upon cooling to room temperature the two phases are separated: the aqueous one is concentrated to a small volume and cooled yielding the desired serine derivative of formula I in the form of its acid addition salt as a crystalline precipitate, while from the organic phase the excess of carbonyl compound, set free by the acid hydrolysis, is recovered.

Further details of the process are to be found in the following representative examples which are given to illustrate the best mode of the invention but are not to be intended as limitative of the scope of the same.

EXAMPLE 1

60.4 g (0.4 mole) of p-nitrobenzaldehyde and 4.8 g (0.02 mole) of methyltributylammonium chloride in 200 ml of $CH_2Cl_2$ are cooled to 5°-7° C. 15 g (0.2 mole) of glycine and 8.8 g (0.22 mole) of sodium hydroxide are dissolved in 30 ml of water and the obtained solution is dropped into the stirred methylene chloride phase in 4 hours. Stirring at 5°-7° C. is continued for further three hours then 35 ml of concentrated hydrochloric acid and 200 ml of water are added. The mixture is heated to 35° C. for 30 minutes and then cooled to 20° C. The two phases are separated and the aqueous one is concentrated by distilling out a volume of 200 g of water. The residue is cooled to 5° C. for 2 hours and the crystalline precipitate which forms is recovered by filtration and dried under vacuum. Yield 42.2 g of threo-(p-nitrophenyl)serine hydrochloride. Considering that the $CH_2Cl_2$ phase contains 34 g of p-nitrobenzaldehyde (as determined by G.L.C. analysis) which is recycled, the percent yield in threo-(p-nitrophenyl)serine hydrochloride is 92% calculated on the p-nitrobenzaldehyde. Further 1.6 g of threo-(p-nitrophenyl)serine hydrochloride and 1.5 g of the erithro form may be obtained from the mother liquors deriving from the filtration.

EXAMPLES 2 TO 4

The reaction has been carried out several times by following the procedures of the foregoing example but using different phase-transfer catalysts and threo-(p-nitrophenyl)serine hydrochloride has been obtained in the following yields:

2—with tetrabutylammoniunm hydrogen sulfate—Yield 87% calculated on p-nitrobenzaldehyde.

3—With methyltributylammonium iodide—Yield 79% calculated on p-nitrobenzaldehyde.

4—With ADOGEN 464 ®—Yield 73%—Calculated on p-nitrobenzaldehyde.

I claim:

1. A process for the production of a serine derivative of the formula

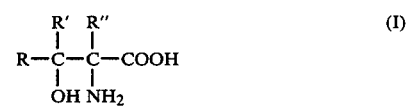

Wherein R stands for phenyl, substituted phenyl of the groups of methylphenyl, methoxyphenyl, ethoxyphenyl, halogenophenyl, hydroxyphenyl, acetylphenyl, nitrophenyl, cyanophenyl, biphenylyl sulfamoylphenyl and methylsulfonylphenyl, tert-butyl or a heteroaromatic mono- to bi-cyclic radical of the group of pyrrolyl, thienyl, furyl, pyridinyl, pyrazinyl, quinolinyl, isoquinolinyl and phthalazinyl, R' represents hydrogen or $(C_1-C_4)$alkyl and R" is hydrogen, $(C_1-C_4)$alkyl or phenyl, which comprises reacting an alkali metal salt of a glycine derivative of the formula

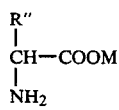
(III)

wherein R" is as defined above and M stands for sodium, lithium or potassium, with two equimolecular proportions of a carbonyl compound of the formula

(II)

wherein R and R' are as defined above, in an aqueous-organic two-phase system in the presence of a concentrated alkali metal hydroxide and an ammonium quaternary salt of the formula $R'_4{}'' N^+ X^-$, wherein each of the four R''', which may be equal or different, represents an alkyl group of from 1 to 20 carbon atoms, and $X^-$ stands for a normal anion which derived from an organic or inorganic acid, at a temperature comprised between 0° and 25° C., hydrolizing the obtained intermediate with a strong mineral acid and recovering the compound of formula I in the form of its acid addition salt by common procedures.

2. The process of claim 1 wherein from about 0.05 to about 0.1 mole of ammonium quaternary salt is employed per mole of the glycine salt.

3. The process of claim 1 wherein the alkali metal hydroxide is employed at least in molar ratio to the catalyst.

4. The process of claim 1 wherein the glycine alkali metal salt is prepared in situ by reacting glycine with an equimolar amount of alkali metal hydroxide.

5. The process of claim 1 wherein the ammonium quaternary salt is selected from methyltributylammonium chloride, methyltributylammonium iodide, tetrabutylammonium hydrogen sulfate and methyltrioctylammonium chloride.

6. The process of claim 1 wherein the organic solvent is selected from methylene chloride, dioxane, tetrahydrofuran, toluene, benzene, chlorobenzene, and carbon tetrachloride.

7. The process of claim 6 wherein the organic solvent is methylene chloride.

8. The process of claim 1 wherein the excess of carbonyl compound is recovered at the end of the reaction.

9. The process of claim 1 wherein R represents one of phenyl, p-acetylphenyl, p-nitrophenyl, and p-methylsulfonylphenyl, and R' and R" are hydrogen.

10. The process of claim 9 wherein R stands for p-nitrophenyl, R' and R" are hydrogen and the configuration is essentially threo.

* * * * *

UNITED STATES PATENT AND TRADEMARK OFFICE
CERTIFICATE OF CORRECTION

PATENT NO. : 4,501,919

DATED : February 26, 1985

INVENTOR(S) : Melvin V. Koch, Ambrogio Magni

It is certified that error appears in the above-identified patent and that said Letters Patent are hereby corrected as shown below:

On the face of the patent, the priority information is missing and should read (under Foreign Application Priority Data) --May 24, 1979 (GB) United Kingdom 7918066--.

At column 1, line 22 the patent reads "and the like.  R'" and should read --and the like, R'--.

At column 4, line 64 the patent reads "mono- to bi-cyclic" and should read --mono- or bi-cyclic--.

Signed and Sealed this

Nineteenth Day of April, 1988

Attest:

DONALD J. QUIGG

*Attesting Officer*      *Commissioner of Patents and Trademarks*